United States Patent

Wang et al.

[11] Patent Number: 6,023,962
[45] Date of Patent: Feb. 15, 2000

[54] RESERVOIR-SLIT RHEOMETER FOR THE VISCOSITY MEASUREMENT OF FAST-REACTING POLYMERS

[75] Inventors: Kuo K. Wang; Sejin Han, both of Ithaca, N.Y.

[73] Assignee: Cornell Research Foundation, Inc., Ithaca, N.Y.

[21] Appl. No.: 09/010,778

[22] Filed: Jan. 22, 1998

[51] Int. Cl.[7] .................................................. G01N 11/08
[52] U.S. Cl. ..................... 73/54.09; 73/54.14; 73/54.39
[58] Field of Search ................. 73/54.04, 54.06, 73/54.07, 54.39, 54.09, 54.11, 54.14

[56] References Cited

U.S. PATENT DOCUMENTS 3,203,225  8/1965  Sieglaff et al. ..................... 73/54.14 X
5,076,096 12/1991  Blyler, Jr. et al. ..................... 73/54.09

FOREIGN PATENT DOCUMENTS 1207559  7/1986  Canada ................................ 73/54.09

OTHER PUBLICATIONS

Blyler, L. L, H. E. Bair, P. Hubbauer, 8 Matsuoka D. S. Pearson, G. W. Poelzing, R. C. Progelhof and W. O. Thierfelder, *A New Approach to Capillary Viscometry of Thermoset Transfer Molding Compounds, Polym. Eng. Sci., 26, (1993).

Dealy, J. M. and Wissbrun, K. F., Melt Rheology and Its Role in Plastics Processing Nostrand Reinhold, New York (1990).

Gonzalez, U., S. F. Shen and C. Cohen, Theological Characterization of Fastreacting Thermosets through Spiral Flow Experiments, Polym. Eng. Sci. 32, 172. (1992).

Halley, P. J. and Mackay, M. E., Chemorheology of Thermosets—An Overview, Polym. Eng. Sci., 36, 593 (1996).

Manzione, L. T., Plastic–Packaging of Microelectronic Devices, Van Nostrand Reinhold, New York (1990).

Nguyen, L. T., A. Danker, N. Santhiran and C. R. Shervin, "Flow Modeling of Wire Sweep during Molding of Integrated Circuits, " ASME Winter Annual Meeting (1992).

Turng, L. S. and V. W. Wang, "On the Simulation of Microelectronic Encapsulation with Epoxy Molding Compound, " 92, SPE RETEC, Raleigh, North Carolina, Nov. 10–12 (199 1).

*Primary Examiner*—Daniel S. Larkin
*Attorney, Agent, or Firm*—Brown, Pinnisi & Michaels, P.C.

[57] ABSTRACT

A viscometer measures the rheological properties of polymers over a wide range of temperature, shear-rate and cure conditions, so that it can be used with extremely fast-changing resinous materials such as fast curing thermosets and fast crystallizing thermoplastics. The viscometer uses a mold made of three plates, clamped together during testing, with the center plate having at least one cavity (reservoir) and a slit from each reservoir to the ambient conditions outside the viscometer. Resin is injected into the reservoir in a short period of time. After filling the reservoir, the sample is heated to a test temperature through heat conduction from the reservoir wall. The heating is rapid because of the small thickness of the reservoir. The rapid filling and heating properties of the apparatus makes the rheology measurement of fast changing polymers possible. The sample is put under pressure by a piston and forced to continuously flow through the slit. At this slit, various measurements, including flow rate, pressure, temperature, and degree of cure are made. Using this instrument, the relationship between the viscosity as a function of temperature, shear-rate, and degree-of-cure can be determined.

25 Claims, 4 Drawing Sheets

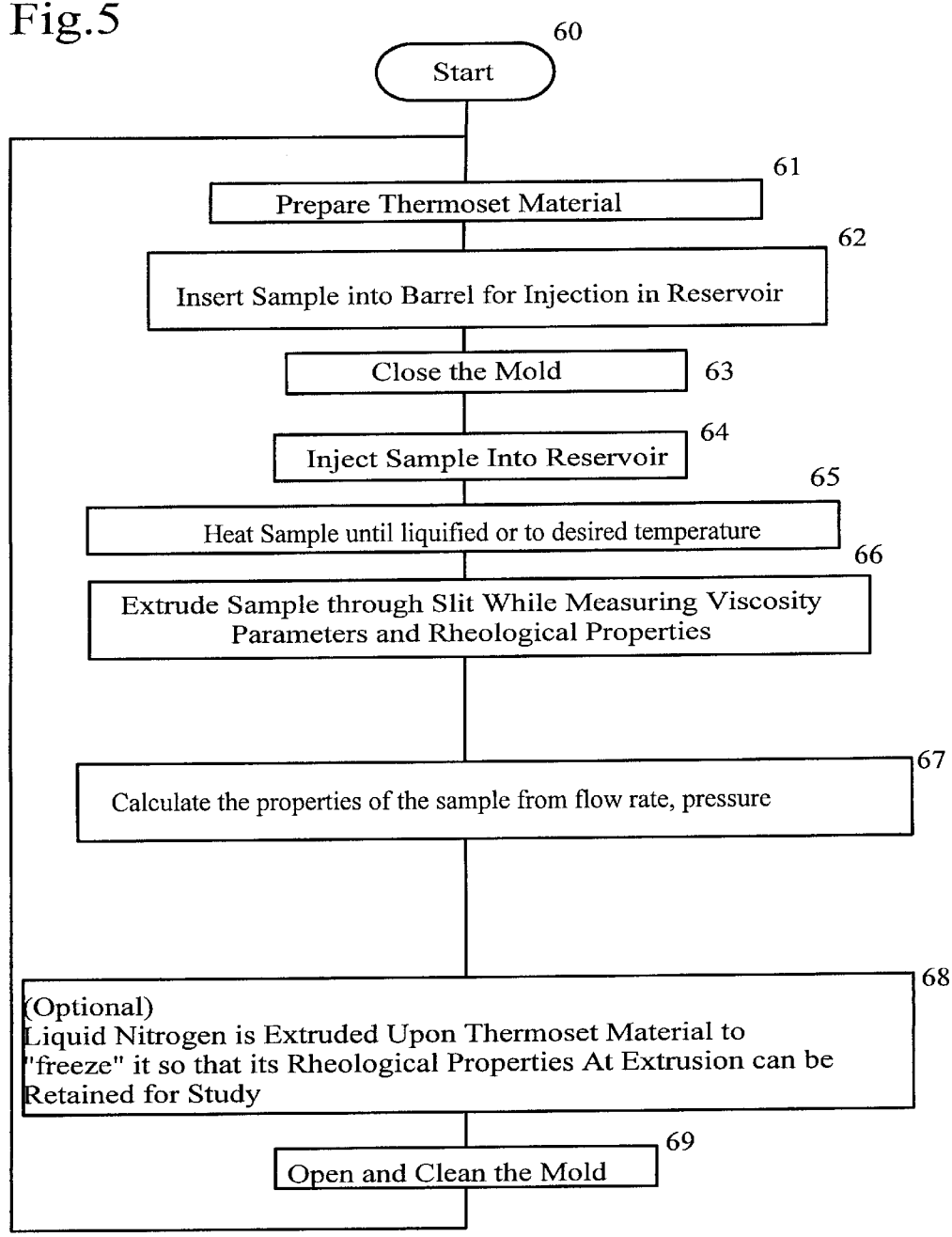

RESERVOIR-SLIT RHEOMETER FOR THE VISCOSITY MEASUREMENT OF FAST-REACTING POLYMERS

FIELD OF THE INVENTION

The invention pertains to the field of characterizing the rheological properties of fast-reacting (or crystallizing) polymers. More particularly, the invention pertains to the creation of a novel apparatus, and associated methods, which allow the reliable measurement of viscosity of fast-changing polymers in highly varied conditions. Such conditions typically exist in manufacturing processes with reactive polymeric materials such as Reactive Injection Molding (RIM), Structural Reactive Injection Molding (Structural RIM), Reactive transfer Molding (RTM), encapsulation of microelectronic chips with Epoxy Molding Compounds (EMCs), and molding with semi-crystalline polymers.

BACKGROUND OF THE INVENTION

The techniques generally used to mold thermosetting resins include compression molding and transfer molding. Compression molding involves placing a resin or polymer sample directly into a mold cavity designed to receive the material. Thereafter, the molding compound is liquefied through a heating process before being formed into the shape of the mold as the mold closes upon itself. After a cooling period, or "curing", and removal from the mold, the resin or polymer material corresponds to the shape of the mold used.

Transfer molding involves placing the molding compound into a separate transfer pot or chamber that applies heat sufficient to liquefy the polymer material. Then, through the application of a transfer plunger, the liquefied polymer, or some set amount of it, is forced to flow into the selected mold cavity, where the mold is then closed so that the polymer is molded and later cured. After curing the mold is opened and the molded polymer form is removed.

In the manufacture of epoxy materials, or other resinous compounds, minor variations in formulation or quality of the ingredients can significantly affect certain qualities of thermoset formulations. Among the qualities that can be dramatically affected are cure time, optimum time for heating prior to injection, speed with which the material should be injected, size of a mold which can be properly filled, integrity of the molding material both during and after molding, and the optimum time to remove molded material from a mold. To evaluate these various qualities of epoxy materials both during the manufacturing process and immediately prior to use, a convenient testing operation is needed.

As computer simulation or Computer-Aided Engineering (CAE) techniques are becoming more essential tools to ensure successful polymer processing, the need for accurate characterization of rheological properties of reactive thermoset materials also becomes very critical. CAE techniques can be used to enhance the quality of industrial polymer molding. Other possibilities for use include the overall optimization of polymer processing, and in the actual design of molds to be used for a specific application. For the proper use of these CAE programs, however, the properties of the polymer materials to be used in the production process must be determined very accurately. Existing instruments and techniques for measuring viscosity at low-temperature and low shear-rate are adequate but most manufacturing processes are under very high shear-rate conditions. The difference in these conditions and the data generated therefrom can quickly lead to problems when quick setting resinous materials are molded at high-shear rates in reliance upon data generated at low shear rates and then extrapolated.

Among the properties that must be determined for polymer materials, viscosity is most important. Viscosity is a measure of the energy dissipation and consequent generation of stress in a fluid, often described, and measured, as flow resistance. The viscosity as a function of temperature of a resinous material to be used in the molding process plays a very important role in the determination of the properties of the eventual product. The viscometer disclosed herein uses quantitative measurements of viscosity, not only as a function of temperature, but also shear rate and the rate of cure in order to determine the exact characteristics of the sample compounds.

There are several methods that are currently being used for the rheology measurement of fast-reacting thermosets. Among them, the parallel-plate viscometer is the most widely used device (Halley and Mackay, 1996). A typical parallel-plate viscometer has two parallel circular plates separated by a specified distance, with a sample inserted between the plates. One plate is connected to a motor which rotates the plate, while the other plate is connected to a transducer, whereby the torque is measured. The rheology of the sample is determined from the applied rotation speed and the measured torque.

Although the parallel-plate viscometer, as found in the prior art, has several advantages, it also has significant limitations. The advantages include small sample size, the ease of cleaning the test device, and the capability of testing at various modes. Perhaps the most significant limitation demonstrated by parallel-plate viscometers is that the range of shear rates of the sample polymer which can be measured in this type of viscometer are rather small. This limitation is similar to other instruments in the prior art whose design did not allow accurate determination of physical characteristics of the thermoset materials at extreme conditions, which are generally the type of conditions most often encountered in today's industrial processes.

Since shear rates in extreme conditions, i.e., high shear rates, cannot be measured by the parallel-plate type viscometers generally in use, there has been an effort made to use the information collected at low shear rates to generate more complete data curves by extrapolation. Since this data was based on extrapolation, it was not, and could not be made, entirely reliable.

Another point that should be made about the inadequacy of the data generated through the use of the parallel-plate viscometer is that the measurement of viscosity of fast-curing thermoset materials at high temperatures is not practical or accurate due to the significant time delay experienced in heating the sample. Simply put, the time it takes for the materials to reach the equilibrium temperature with this instrument is often longer than it takes for these materials to "set" and begin their cure. It is these newer and faster reacting materials that are becoming more popular in manufacturing today, and for them the data generated by the parallel-plate viscometer is not as accurate as it should be because the extrapolation of data from low temperature to high temperature is required.

When using known technologies to obtain the viscosity at shear rates and temperatures that more accurately reflect the extreme conditions of heat and pressure that are routine in current industrial processing today a new process is needed. Too much reliance on extrapolation can lead to errors in both calculation and production.

Another popular method for viscosity characterization of resinous materials, and specifically Epoxy Molding Compounds (EMC's), is through the use of the "spiral flow test" (Gonzalez et al., 1992). In the spiral flow test, a sample polymer compound is forced through the entrance and into a spiral shaped mold cavity. This usually occurs at approximately 300±5° F., but can be altered to suit the specific polymer material used. Generally, there is an approximate pressure of 500 psi. applied to a sample, as calculated from the surface area of the piston used. The distance the compound flows into the spiral mold is then measured. The distance of this flow is primarily a function of the viscosity of the compound when in liquid state, and the time which it requires to "set" or gel.

Typically molds used in industry have a runner or trough-like cavity leading from the injection opening to a gate which gate is in some way connected to the main molding cavity. The spiral flow test, however, creates the equivalent of a spiral runner. This extruded ribbon of sample or "runner" is a polymer which has no equivalent in the vast majority of typical industrial molding products. Accordingly, the flowing tip of molding material in a spiral flow mold does not share the same flow characteristics or shear rates of the same or similar material used in a conventional mold to produce typical products. The excessive length of the runner and the varying radius of the spiral also contribute to the problem of using the data generated from the spiral flow test as indicative of the flow characteristics of actual mold products.

Also, the spiral flow test fails to conveniently allow determination of optimal times for injection and curing of different epoxy molding materials. While the utility of the spiral flow test is demonstrated in its simplicity, there are problem in addition to the problems already outlined. These problems include the fact that this method requires extensive numerical simulations to back out the viscosity parameters from the melt-front trace and/or pressure trace measurements. Compounding this is the fact that this data often does not produce converged values, a factor which will often then lead to erroneous results.

An alternate method used to measure the viscosity of thermoset materials is through the use of capillary instruments. Capillary instruments share the disadvantage of requiring a significant dwell time which makes measurement at high temperatures difficult, as well as the difficult and costly cleanup of the setting materials used (Blyler et al., 1986).

As discussed above, none of the prior devices or methods mentioned above is able to obtain data at the whole range of the normally utilized industrial processing ranges.

The apparatus and associated methods of the present invention are designed to quantifiably measure the rheology of thermoset materials as accurately as possible throughout the entire range of shear rate, temperature, and degree of cure often encountered in modern industrial processes. Thus, the basic design of this device is itself a departure from the prior art. Moreover, this device improves upon the prior art through its ability to allow the accurate and reliable testing of extremely fast reacting or crystallizing materials, quite beyond the reach of the prior art, as already discussed.

SUMMARY OF THE INVENTION

Briefly stated, the viscometer of the present invention is capable of measuring rheological properties of polymers where the rheology changes in a very short time. The apparatus uses a three-part mold having an internally heated reservoir. A piston rapidly injects the sample to be tested into a reservoir in the mold (possibly in a solid, particulate state) and the sample is heated in the reservoir by heat conduction from the reservoir wall. Because the reservoir is thin, heating to a test temperature can be done very quickly. When the sample fills the reservoir completely, the piston is again actuated, at a slower speed, to force the sample through a small aperture or a "slit." By measuring the flow rate and pressure drop across the slit and knowing the dimensions of the reservoir and slit, the rheology of the sample can be calculated.

Optionally, liquid nitrogen can be used to stop the cure of an extruded sample at the exit of the slit, thereby allowing better characterization of the curing state of a sample.

The invention generates reliable rheology of fast reacting (or crystallizing) polymers in all processing conditions, including extreme ones, thereby eliminating the need to extrapolate data. The viscometer disclosed herein can measure viscosity at a very wide range of shear rates and temperatures. It can also monitor viscosity at a wide degree of cure-state (i.e., from uncured state to gel point). It also has other advantages such as capability of measuring pressure dependence of viscosity, as well as the ease of cleaning the apparatus after a sample has been tested.

BRIEF DESCRIPTION OF THE DRAWINGS

FIG. 5 shows a flowchart of the method of the invention.

DESCRIPTION OF THE PREFERRED EMBODIMENT

Principles and Protocols for Making Proper Measurements

Figure 1:
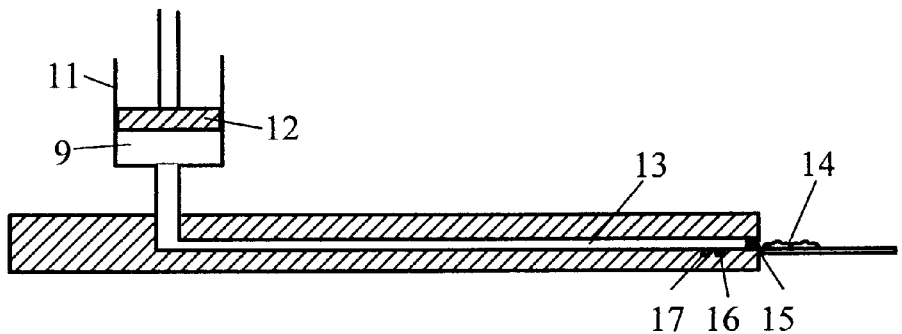
FIG. 1 shows a simple schematic of the novel viscometer as in the invention.

FIG. 1 shows how the sample (9) is initially placed in the barrel (11), thereafter the sample is injected into the reservoir (13) by the downward movement of the piston (12). The period of injection to fill reservoir (13) is as short as possible. The sample (9) is heated in the internal reservoir (13) to the testing temperature through heat conduction from the reservoir walls. Reservoir (13) is preferably thin so that the sample reaches the test temperature in a short time. After completely filling the reservoir, the sample (9) in the reservoir (13) is extruded through the slit (15) at a slower speed by the action of the piston (12). The pressure drop of the sample (9) in the slit (15) is measured by a pressure transducer (16), such as model PT465XL from Dynisco having a maximum pressure range of 10,000 psi, while the sample flows through the slit (15). Flow rate can be obtained by measuring the ram speed. From the measured quantities and assuming Newtonian, isothermal, and uniformly curing flow in the slit (15), the viscosity and shear rate can be obtained from the following equations (Dealy and Wissbrun (1990)):

$$\eta = \frac{4\Delta pch^3}{3QL} \qquad (1)$$

$$\dot{\gamma} = \frac{3Q}{4ch^2} \qquad (2)$$

where η is the viscosity, γ̇ is the shear rate, Δp is the pressure drop, Q is the flow rate in the slit (15), h is the half-thickness of the slit (15), L is the length of the slit (15), and c is the half-width of the slit (15), assuming that c is much greater than h. The degree of cure of the sample (9) at each time during viscosity measurement can be obtained by measuring the degree of cure of the sample (9) after quenching it as soon as it passes the slit (15). Alternatively, it can be obtained by simulating the viscosity measurement process using curing kinetics data measured separately.

In actual situations, the flow is not Newtonian and a numerical simulation can be used to correct for the error resulting from this assumption.

The numerical simulation of the viscosity measurement process from the data collected can be performed using the following approach. In the current apparatus according to the present invention, the thickness of the cavity is very small compared to the width and the inertia effect is small compared to the viscous effect. In this case, it is possible to use the Hele-Shaw approximations for a given test as in Turng & Wang (1993). With these conditions, the following set of equations is obtained:

$$\frac{\partial \rho}{\partial t} + \frac{\partial (\rho u)}{\partial x} + \frac{\partial (\rho v)}{\partial y} + \frac{(\rho w)}{\partial z} = 0 \qquad (3)$$

$$0 = \frac{\partial}{\partial z}\left(\eta \frac{\partial u}{\partial z}\right) - \frac{\partial p}{\partial x} \qquad (4)$$

$$0 = \frac{\partial}{\partial z}\left(\eta \frac{\partial v}{\partial z}\right) - \frac{\partial p}{\partial y} \qquad (5)$$

$$\rho C_p\left(\frac{\partial T}{\partial t} + u\frac{\partial T}{\partial x} + v\frac{\partial T}{\partial y}\right) = \frac{\partial}{\partial z}\left(k\frac{\partial T}{\partial z}\right) + \eta \dot{\gamma}^2 + \frac{d\alpha}{dt}H \qquad (6)$$

where p is the pressure, T is the temperature, α the degree of cure, and u, v, and w are the velocity components in the x, y, and z directions, respectively (where z corresponds to the gap direction). Further, ρ is the density, $C_P$ is the heat capacity, k is the thermal conductivity, and H is the heat generation due to curing.

In the above equations, equation (3) is termed the "continuity equation", equations (4) and (5) are termed the "force balance equations", while equation (6) is termed the "energy equation."

These equations must be used together with a curing-kinetics equation for a solution to be derived. Once this is done, the equations can be solved numerically by the finite element method. The wall shear rate can be obtained from the simulation. The wall shear stress in the slit (15) can be obtained from the experimentally measured pressure drop across the slit (15) by the following equation:

$$\tau_w = \frac{\Delta ph}{L} \qquad (7)$$

From the wall shear stress and wall shear rate $\dot{\gamma}_w$, the corrected viscosity can be obtained by:

$$\eta_w = \frac{\tau_w}{\dot{\gamma}_w} \qquad (8)$$

Mold

Figure 3:
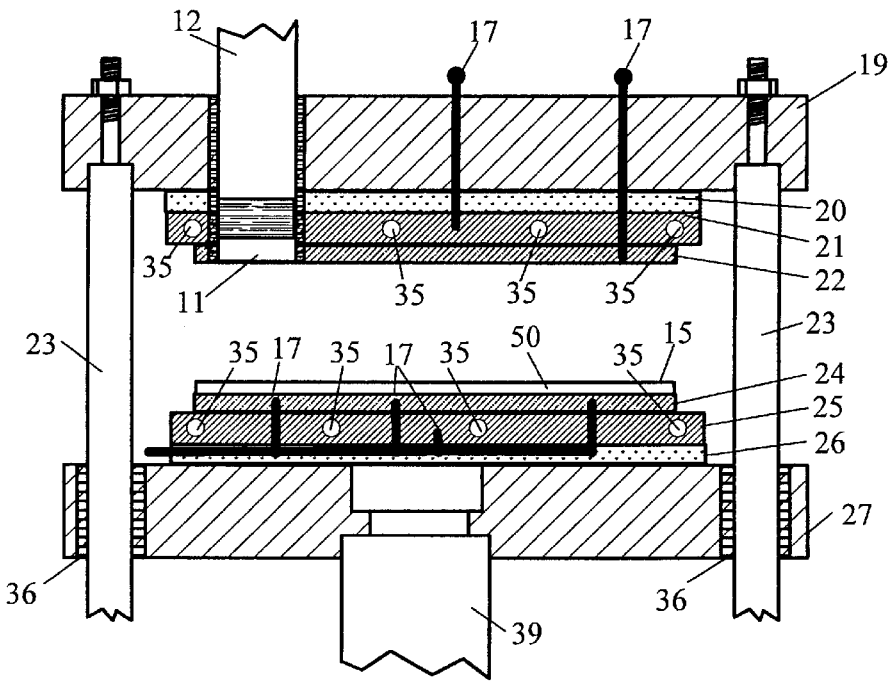
FIG. 3 shows a detailed depiction of a slit rheometer, near the mold, designed for the measurement of viscosity of reactive polymers.

Referring to FIG. 3, the mold is made up of three plates (top (22), middle (50), and bottom (24) plates). This construction facilitates the cleaning of the reservoir or reservoirs which were used for sample testing. The top mold plate (22) and the bottom mold plate (24) act as top and bottom walls for the sample reservoirs present in a given embodiment of the invention. The middle plate (50) contains a reservoir (41) and slit (15). The internal reservoir (41) thus created is designed to hold a given sample during testing. For fast temperature equilibrium to be reached, which is necessary for fast curing materials, a thickness of middle plate (50) is constructed to be small. The characteristic thermal equilibrium time in the reservoir, i.e., the time to reach 63% of the final temperature from the initial temperature, is roughly $$\frac{h^2}{\alpha_t},$$

where h is the half-thickness of the reservoir and $\alpha_t$ is the thermal diffusity of the sample to be tested. Therefore, by making h small, the characteristic time can be reduced to a very short time. The exact dimensions of reservoir (41) and slit (15) depends on the polymer being tested. For epoxy molding compounds, reasonable dimensions of reservoir (41) are approximately 300 mm (length) by 100 mm (width) by 1.5 mm (thickness), while the dimensions of slit (15) are approximately 20 mm (length) by 4 mm (width) by 0.4 mm (thickness). The total system is approximately 2 m (height) by 1 m (width) by 0.5 m (depth).

The slit (15) is where the flow is directed by the piston (18) and where the viscosity measurement is taking place. By measuring the flow rate and the pressure drop at the slit (15), viscosity and shear rate can be determined. The slit size is made sufficiently small so that the pressure drop in the slit (15) is much larger than those in other regions of the reservoir (41).

Figure 4A:
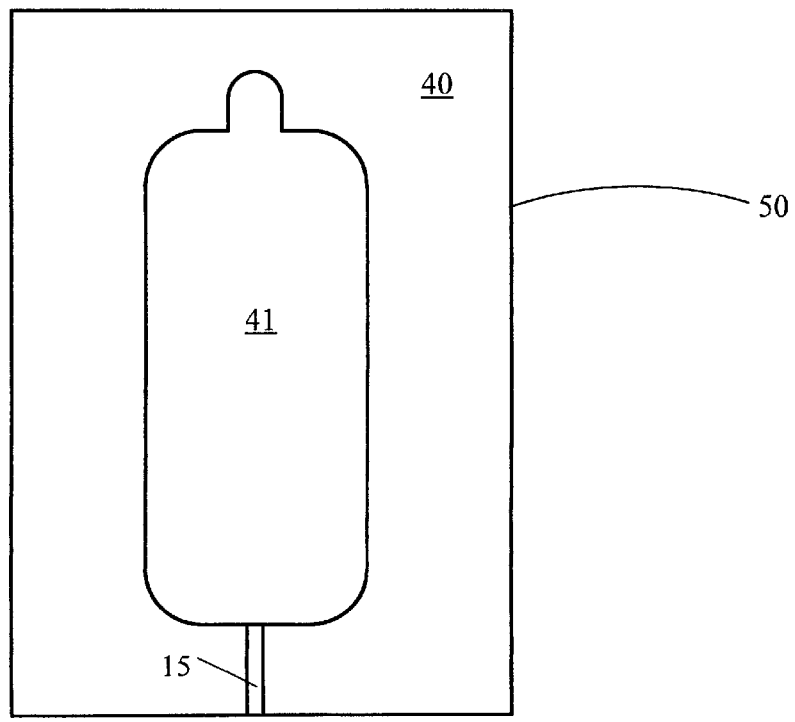
FIG. 4a shows the configuration of the middle mold plate with a single reservoir slit.
Figure 4B:
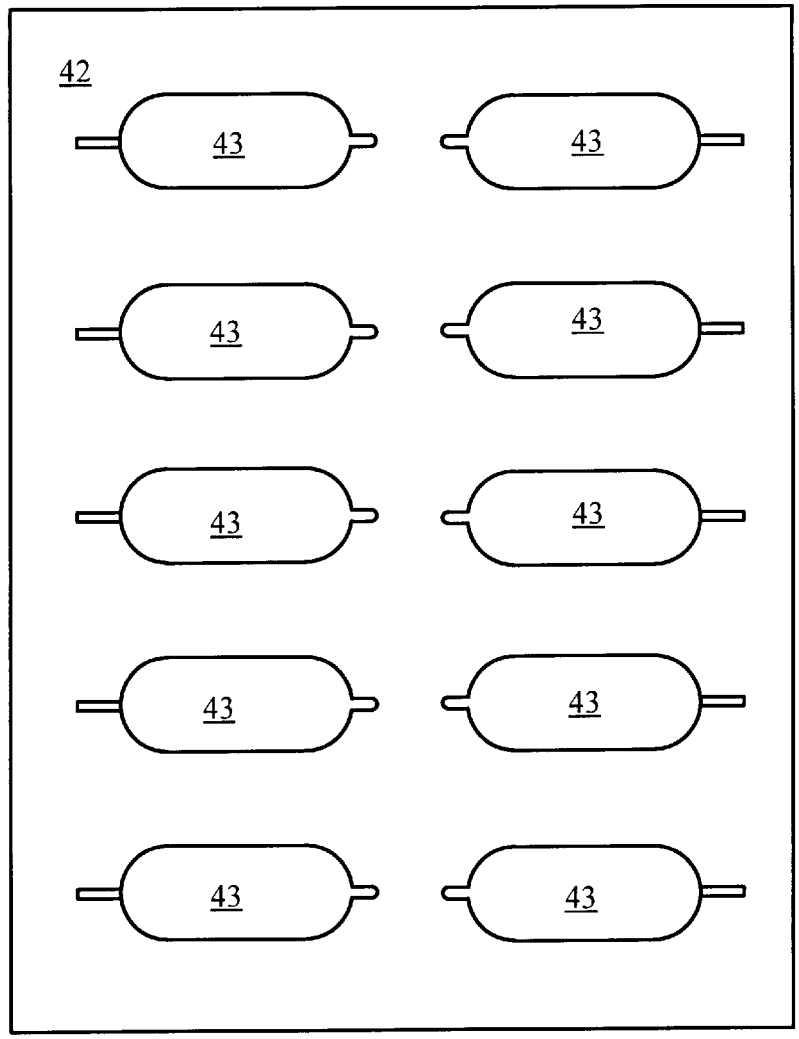
FIG. 4b shows the configuration of the middle mold plate with multiple reservoir slits.

FIG. 4a depicts an example of the middle-plate design (50) where a single reservoir (41) and a single slit (15) is located in the middle plate. In the single reservoir version of the apparatus, viscosity can be measured for only one set of conditions in one run. In FIG. 4b, a middle plate (42) with multiple reservoirs (43) and slits is shown. A reasonable number of reservoirs is about 20. In the multi-reservoir design, the motive force for each sample is supplied by an individual piston drive system (18). Through the mechanical design put forward herein, the pistons (12) can be activated simultaneously at the same speed. With several different slit geometries, one can obtain viscosity data at several different shear rates simultaneously. Alternatively, data concerning the entrance effect on viscosity can be collected through the use of slits that have different lengths but the same sectional dimension.

Heating System

This system is designed to carefully maintain the mold plate (40) as shown in FIG. 4(a) at a given testing temperature. Possible testing temperatures range from approximately room temperature to about 350° C. The heating system as shown in FIGS. 3 and 4(a) consists of two heating plates, top and bottom heating plates (21), (25) respectively, with several heating elements (35) being inserted into each heated plate. First and second layers of insulation (20), (26) are put around each of the heating elements (35) present to isolate a given high temperature region from the rest of the system, other than the reservoir (41) to be heated. The heating element can be a cartridge heater.

Clamping System

Figure 2:
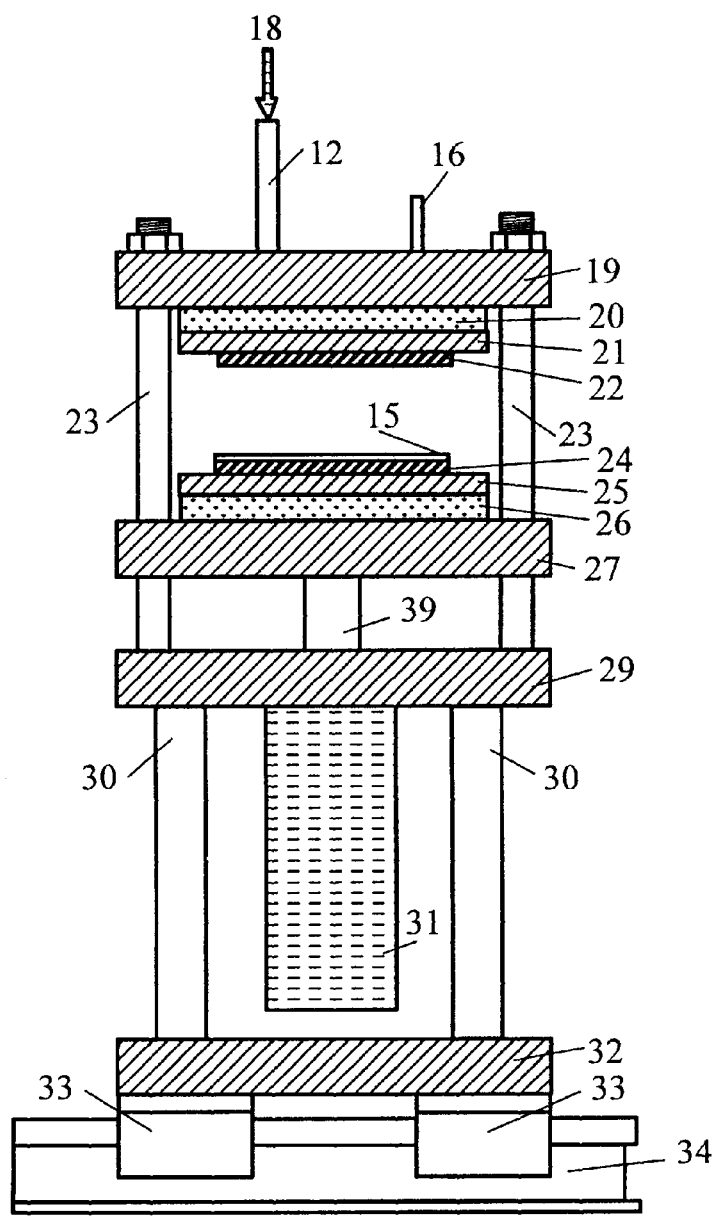
FIG. 2 shows a detailed drawing of the overall arrangement of the viscometer.

The clamping system was designed to enhance the ease of opening and closing the mold and to securely maintain clamping forces during measurement. The clamping force can be achieved by using double acting hydraulic cylinder (31). In FIG. 2, the clamping system consists of hydraulic cylinder (31), and frame plates #1 through #4 (19), (27), (29), and (32) respectively and shafts for plate movement (23), slidably positioned within channels (36), and (30). Frame plate #1 (19) is a fixed plate which holds the top mold assembly. Frame plate #2 (27) is a movable plate which moves by means of the hydraulic cylinder (31). This opens and closes the mold. Frame plate #3 (29) is a fixed plate onto which is mounted the body of the hydraulic cylinder (31), the bottoms of the four upper shafts, and the tops of the four lower shafts. Frame plate #4 (32) is a fixed plate at the bottom (34) of the instrument. It supports the entire apparatus through the four lower shafts which is attached to it at base supports (33).

Injection System

This system is designed to enable the development of a controlled force with which to move the sample during the testing. The mechanical elements consist of a piston (12) fitting tightly in a barrel (11) for holding the sample and a drive system (18) for applying pressure to the piston. Piston (12) preferably has a pressure range up to about 10,000 psi material pressure. In those versions of the invention with more than one reservoir (43), more than one piston (12) would be required. As stated above, the piston drive system (18) can include a hydraulic cylinder or an electric cylinder and must be capable of supplying enough force, quickly enough so that various speeds of movement for the sample to be tested are possible. The minimum that could be provided would be two levels of speed, one for reservoir filling and one for testing. High speed is needed when filling the reservoir (41), but a much lower speed is needed after the filling of the reservoir (41) is complete when testing has begun. The velocities in a low speed regime can be varied to achieve different shear rates. The range of speed of piston (12) is preferably from about 0.01 mm/s to about 100 mm/s, with the range being easily controlled by a control device such as a servo-valve. Because of the large speed range, a translation system similar to those used in tensile testing machines can be used. The barrel (11) is a tube from which the material sample can be forced into a reservoir (41) or mold cavity by means of a piston (12). The disclosed invention provides a wide range of speeds and respective forces as necessary for that piston (12).

Data Acquisition and Processing System

The data required for acquisition is the pressure, mold temperature, and flow rate of the sample, without which the equations laid out above are useless for measurement purposes. Pressure measurement is done by putting a pressure transducer(s) (16) in the reservoir (13) in front of the slit (15). Mold temperature is measured by inserting a thermocouple device (17) in the mold near the slit (15). The flow rate is obtained by measuring the piston speed and multiplying by the surface area of the piston (12) in contact with the sample (e.g. the surface of the piston whose force is pushing the sample through the barrel (11)). This measurement assumes the incompressibility of the sample. The data processing system is designed to generate viscosity and shear rates from the measured pressure and flow rates. From the measured pressure and flow rate, the viscosity and shear rate of the material can be calculated by first assuming the flow in the slit to be Newtonian, isothermal, and of uniform cure. This assumption is later corrected for by calculating the wall shear rate at the slit (15) using a numerical simulation, as discussed above. A software program developed that is based on a generalized Hele-Shaw approximation can be used for this purpose. This computer software simulation program can enable the generation of true viscosity and shear rate information from the measured experimental data, and will thereby facilitate data processing.

Operation of the Viscometer

Referring to the flow chart of FIG. 5, the method of the invention is as follows:
Start (60): Prepare the Sample for Testing (61) and Place it in the barrel (62)
The sample (9), usually in solid particulate form, is fed into the injection barrel (11). If required, and if the composition of the sample (9) allows the sample (9) to be pre-heated without sacrificing its ability to be tested accurately, the sample (9) can be pre-heated separately to a temperature just above the glass-transition temperature and formed thereafter for injection through the barrel (11).
Closing the Mold (63)
The mold is closed, and clamped by moving the clamping system piston (39), forcing the movable plates (25)–(27) upward. This holds the top (22), middle (50) and bottom (24) mold plates together firmly against the force of the injected sample.
Injecting the Sample (64)
The sample is then rapidly injected into a heated reservoir in the mold by moving the piston at high speed. The filling of the reservoir (13) has to finish as soon as possible, i.e., in a much smaller period than the gel time of the resin at the testing temperature. Typical filling time of the reservoir (13) is less than 1 second.
Heating the Sample (65)
The sample is then heated in the reservoir. The reservoir thickness (preferably about 1 mm) is very small, which facilitates a very fast rise of temperature to the testing temperature, such that the resin sample may be heated to the preselected temperature in less than about three seconds. With most resins, the material sample can reach the testing temperature in several seconds.
Extrusion (66)
The sample is then extruded through a slit (15) by the action of the sample piston (12). The piston speed at this stage is much slower than that of the injection piston (12) during the initial reservoir filling stage. The pressure within the reservoir is measured by means of melt pressure sensor (s) (16) in the reservoir wall or walls. The flow rate is obtained by measuring the ram speed and multiplying it by the area of the piston. For samples whose rheology depends on the history (such as thermosetting polymers), only the sample that fills the reservoir initially needs to be extruded for testing. This is because a sample that enters the reservoir late will have a different temperature history from one that enters the reservoir initially. This can be assured by making the volume of the reservoir at least 1.5 times bigger than the volume of the sample used in the testing.

Calculation of Sample Characteristics (67)

Based on the known die dimensions of the slit (15) and the measured temperature, pressure drop, and flow rate of the sample in the slit (15), the material's viscosity at a set temperature and shear rate is calculated. Again assuming Newtonian flow, the viscosity and shear rate can be calculated by using equations (1) and (2). Measurements are made continuously over time until curing occurs and the viscosity of the sample exceeds the instrument capability. The degree of cure of the sample can be obtained either by measuring the degree of cure of the extrudate after quenching, as will be described later, or by simulating the viscosity measurement process using curing kinetics parameters independently measured. Thus, from one sample, a single curve of viscosity versus time can be obtained at a given shear rate and temperature.

Apply Liquid Nitrogen to Extruded Material (68)

Optionally, liquid nitrogen can be used to stop the cure of an extruded sample, which allows better characterization of the degree of cure of a sample. Sections of the solid extrudate from the slit are then used to measure the degree of cure on a differential scanning calorimeter (DSC).

Opening the Mold (69)

The mold is opened by moving the movable plate downward, thereby disengaging the plates. After cleaning (60), the viscometer is ready for the next measurement.

Repeat at Various Parameters

The testing can be performed at different temperatures and shear rates, and possibly other conditions. From this, the viscosity can be obtained as a function of shear rate, temperature, and degree of cure. Data correction can be done using a simulation of the viscosity measurement process.

One of the main distinguishing features of the current instrument is the use of a thin reservoir for sample heating. For example, by using a reservoir of approximately 1 mm thickness, typical epoxy molding compound can be heated to the test temperature in about 2–3 seconds. In addition, because the heating is mainly through heat conduction from the mold wall, overheating is easily avoided. Another distinguishing feature is fast filling of the reservoir. This feature ensures that all the samples that fill the reservoir initially have almost the same thermal history. This makes the testing at high temperatures possible for fast-reacting polymers.

Although the above description is written for fast curing thermoset material, such as, for example, epoxy molding compound, the method and apparatus of the invention can also be used for other polymers where the rheology changes in a very short time, such as with crystalline polymers.

Accordingly, it is to be understood that the embodiments of the invention herein described are merely illustrative of the application of the principles of the invention. Reference herein to details of the illustrated embodiments are not intended to limit the scope of the claims, which themselves recite those features regarded as essential to the invention.

Literature Cited

1. Blyler, L. L., H. E. Bair, P. Hubbauer, S. Matsuoka, D. S. Pearson, G. W. Poelzing, R. C. Progelhof and W. G. Thierfelder, "*A New Approach to Capillary Viscometry of Thermoset Transfer Molding Compounds,*" *Polym. Eng. Sci.*, 26, (1993).
2. Dealy, J. M. and Wissbrun, K. F., *Melt Rheology and Its Role in Plastics Processing*, Nostrand Reinhold, New York (1990).
3. Gonzalez, U., S. F. Shen and C. Cohen, "*Rheological Characterization of Fastreacting Thermosets through Spiral Flow Experiments,*" *Polym. Eng. Sci.*, 32, 172. (1992).
4. Halley, P. J. and Mackay, M. E., , "*Chemorheology of Thermosets—An Overview,*" *Polym. Eng. Sci.*, 36, 593 (1996).
5. Manzione, L. T., *Plastic Packaging of Microelectronic Devices*, Van Nostrand Reinhold, New York (1990).
6. Nguyen, L. T., A. Danker, N. Santhiran and C. R. Shervin, "*Flow Modeling of Wire Sweep during Molding of Integrated Circuits,*" *ASME Winter Annual Meeting* (1992).
7. Turng, L. S. and V. W. Wang, "*On the Simulation of Microelectronic Encapsulation with Epoxy Molding Compound,*" 92, SPE RETEC, Raleigh, N.C., Nov. 10–12 (1991).

What is claimed is:

1. An apparatus for testing the rheological properties of resins at a wide range of shear rate, degree of cure, and temperature, comprising:
   a) a mold comprising:
      i) a first plate having upper and lower surfaces and at least one orifice for the passage of the resins from the upper surface to the lower surface;
      ii) a second plate of a predetermined thickness located below said first plate in alignment therewith, having at least one central opening, the size of the opening and the thickness of the second plate being selected to form a mold cavity, each central opening being located beneath an orifice in the first plate: the second plate also having a slit of predetermined size communicating from each central opening through a side of the second plate; and
      iii) a third plate located below and in alignment with said second plate, having upper and lower surfaces;
   b) means for clamping the first, second, and third plates together such that the lower surface of the first plate and the upper side of the third plate enclose the opening in the second plate, forming the mold cavity;
   c) injection means for supplying the resin under a controlled pressure, having an output connected to at least one of the orifices in the first plate; and
   d) means for heating the resin in the mold cavity to a preselected temperature;
   such that the injection means injects the resin under a controlled pressure through an orifice in the first plate into the mold cavity, the heating means heats the resin to the preselected temperature, and the resin flows out of the mold cavity through the slit.

2. The apparatus of claim 1, in which the injection means comprises:
   a) a barrel, having an open top, solid walls and a bottom having an aperture therein, the walls enclosing a volume sufficient to contain a sample of resin and the aperture forming the output of the injection means;
   b) a piston, fitting tightly within the walls of the barrel, capable of sliding within the barrel to press upon the sample therein, forcing the sample through the aperture in the bottom of the barrel; and
   c) drive means for applying one of a controlled pressure and controlled speed upon the piston.

3. The apparatus of claim 2, in which the drive means comprises a hydraulic cylinder.

4. The apparatus of claim 2, in which the drive means comprises an electrical cylinder.

5. The apparatus of claim 2, further comprising means for measuring the velocity of movement of the piston.

6. The apparatus of claim 1, wherein:
   a ratio of a thickness of the slit to a thickness of the reservoir is less than about 0.25;
   a ratio of a width of the slit to the thickness of the slit is greater than about 10; and
   a ratio of a length of the slit to the thickness of the slit is greater than about 50.

7. The apparatus of claim 1, wherein the thickness of the second plate is such that the resin in the cavity is heated to the preselected temperature in less than about three seconds.

8. The apparatus of claim 1, in which the resin is initially in a solid particulate state.

9. The apparatus of claim 1, in which the resin is initially in a liquid state.

10. The apparatus of claim 1, in which the means for clamping the first, second, and third plates together comprises:
   a) a hydraulic cylinder having a hydraulically actuated piston which applies a force in response to the introduction of hydraulic fluid under pressure into the cylinder; and
   b) a fixed structure;
      the first, second, and third plates being located between the hydraulically actuated piston and the fixed structure, such that introducing hydraulic fluid into the hydraulic cylinder causes the piston to apply a force, clamping the first, second, and third plates between the piston and the fixed structure.

11. The apparatus of claim 1, further comprising at least one pressure sensor means for measuring the pressure of the resin in the mold cavity.

12. The apparatus of claim 1, further comprising at least one temperature sensor for measuring the temperature of the resin in at least one mold cavity, located near the slit.

13. The apparatus of claim 1, in which the means for heating comprises heating elements in said first and third plates.

14. The apparatus of claim 1, in which the means for heating comprises a heating element between the clamping means and the first plate, in contact with the upper surface of the first plate.

15. The apparatus of claim 1, in which the means for heating comprises a heating element between the clamping means and the third plate, in contact with the lower surface of the third plate.

16. The apparatus of claim 1, in which there are a plurality of central openings in the second plate and a plurality of orifices in the first plate, forming a plurality of mold cavities, such that each said internal reservoir is capable of heating, and testing a given resin sample such that viscosity and other relevant parameters can be measured.

17. The apparatus of claim 1 wherein the material to be tested is an epoxy compound.

18. The apparatus of claim 1 wherein the material to be tested is a reactive polymeric compound.

19. The apparatus of claim 1 wherein the material to be tested is a crystallizing polymer.

20. The apparatus of claim 1, further comprising an insulation layer around the means for heating the resin.

21. A method of measuring rheology of a sample in a viscometer comprising a barrel for containing the sample, a piston located in the barrel for forcing the sample out of the barrel into a heated reservoir under pressure, the reservoir comprising a cavity bounded by at least one wall and a slit between the cavity and ambient conditions, comprising the steps of:
   a) placing a sample in the barrel;
   b) filling the cavity quickly by a rapid movement of the piston;
   c) once the cavity is full, heating the sample through conduction from said reservoir wall;
   d) moving the piston at a lower speed than in step (b), causing the sample to be ejected from the cavity through the slit;
   e) measuring the pressure drop between the cavity and ambient and also measuring the flow rate of the sample through the slit;
   f) continuing the injection until the sample gels; and
   g) calculating the viscosity $\eta$ of the sample from the pressure drop and flow rate using the formula $$\eta = \frac{4\Delta pch^3}{3QL},$$

where $\Delta p$ is the pressure drop, Q is the flow rate in the slit, h is the half-thickness of the slit, L is the length of the slit, and c is the half-width of the slit.

22. A method of measuring rheology of a sample in a viscometer comprising a barrel for containing the sample, a piston located in the barrel for forcing the sample out of the barrel into a heated reservoir under pressure, the reservoir comprising a cavity bounded by at least one wall and a slit between the cavity and ambient conditions, comprising the steps of:
   a) placing a sample in the barrel;
   b) filling the cavity quickly by a rapid movement of the piston;
   c) once the cavity is full, heating the sample through conduction from said reservoir wall;
   d) moving the piston at a lower speed than in step (b), causing the sample to be ejected from the cavity through the slit;
   e) measuring the pressure drop between the cavity and ambient and also measuring the flow rate of the sample through the slit;
   f) continuing the injection until the sample gels; and
   g) calculating the shear rate $\dot{\gamma}$ of the sample from the pressure drop and flow rate shear rate using the formula $$\dot{\gamma} = \frac{3Q}{4ch^2}$$

where Q is the flow rate in the slit, h is the half-thickness of the slit, and c is the half-width of the slit.

23. The method of claim 22, in which a wall shear rate $\tau_w$ is calculated using the formula $$\tau_w = \frac{\Delta ph}{L},$$

where $\Delta p$ is the pressure drop, h is the half-thickness of the slit, and L is the length of the slit.

24. The method of claim 23, in which the corrected viscosity $\eta_w$ is calculated using the formula $$\eta_w = \frac{\tau_w}{\dot{\gamma}}.$$

25. A method of measuring rheology of a sample in a viscometer comprising a barrel for containing the sample, a piston located in the barrel for forcing the sample out of the barrel into a heated reservoir under pressure, the reservoir comprising a cavity bounded by at least one wall and a slit between the cavity and ambient conditions, comprising the steps of:
   a) placing a sample in the barrel;
   b) filling the cavity quickly by a rapid movement of the piston;
   c) once the cavity is full, heating the sample through conduction from said reservoir wall;

d) moving the piston at a lower speed than in step (b), causing the sample to be ejected from the cavity through the slit;

e) measuring the pressure drop between the cavity and ambient and also measuring the flow rate of the sample through the slit; and f) continuing the injection and applying liquid nitrogen to the sample as it is extruded from the slit, instantly stopping the cure of said extruded sample.

\* \* \* \* \*